US00PP37379P2

(12) United States Plant Patent
Hansen

(10) Patent No.: US PP37,379 P2
(45) Date of Patent: Apr. 21, 2026

(54) ***ASTILBE* PLANT NAMED 'Dragon's Lair'**

(50) Latin Name: ***Astilbe* hybrid**
Varietal Denomination: Dragon's Lair

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,866

(22) Filed: Oct. 14, 2025

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./407
See application file for complete search history.

*Primary Examiner* — Susan McCormick Ewoldt

(57) ABSTRACT

A new and distinct hybrid of *Astilbe* plant named 'Dragon's Lair' has mounded habit producing purplish-grey triternate foliage that is topped with tall, upright, stiff, dark-burgundy, upright, and densely branched panicles with numerous, densely-clustered rosy-purple flowers. The new plant is a rapid grower, shows heat and sun tolerance, and is useful in the landscape, in containers, or as a cut flower.

2 Drawing Sheets

Botanical denomination: *Astilbe* hybrid.
Variety denomination: 'Dragon's Lair'.

STATEMENT REGARDING PRIOR DISCLOSURES UNDER 37 CFR 1.77(B)(6)

The earliest offer for sale anywhere in the world of *Astilbe* 'Dragon's Lair' was a private offer to Centerton Nursery by Walters Gardens, Inc. on Oct. 15, 2024. Walters Gardens, Inc. obtained the new plant and information about the new plant directly from the inventor. No plants of *Astilbe* 'Dragon's Lair' have been sold, in this country or anywhere in the world, nor has any disclosure of the new plant been made, more than one year prior the filing date of this application, and such sale or disclosure within one year was either derived directly or indirectly from the inventor and as such would be a 35 U.S.C § 102(b) exception.

BACKGROUND OF THE INVENTION

The present invention relates to a new and distinct cultivar of *Astilbe* in the Saxifragaceae family and given the cultivar name of 'Dragon's Lair'. 'Dragon's Lair' was hybridized by the inventor on Jul. 2, 2018, at a wholesale perennial nursery in Zeeland, Michigan, USA as a cross between *Astilbe* 'Dark Side of the Moon' U.S. Plant Pat. No. 35,461 as the female parent and 'Delft Lace' U.S. Plant Pat. No. 19,839 as the male parent. The single seedling resulting in the name variety was assigned the breeder code 18-28-1 through the trial process.

*Astilbe* 'Dragon's Lair' was first selected in the fall of 2019 and passed final evaluation in the fall of 2021 from among several other seedlings from the same cross and other crosses. 'Dragon's Lair' has been asexually propagated by initially in 2021 by division of the crown at the same nursery in Zeeland, MI followed by sterile shoot tip tissue culture propagation, and the resultant plants of both propagation systems have remained stable and continued to exhibit the same characteristics as the original plant for multiple generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype. The following traits in combination have been repeatedly observed and are determined to be the unique characteristics of 'Dragon's Lair' and distinguish the new cultivar as a new and distinct *Astilbe* plant:

1. Mounded plant habit producing dense panicles with upright branchlets;
2. Emerging leaves are burgundy and develop into purplish-grey;
4. Upright, densely-branched, dark-burgundy panicles;
5. Numerous, densely-clustered, deep mauve-colored flower buds that open to densely-clustered rosy-purple flowers on heavily-branched stems;
6. Rapid growth and good garden performance.

The nearest comparison *Astilbe* plants known to the inventor besides the parents include: 'Amber Moon' U.S. Plant Pat. No. 26,028, 'Chocolate Cherry' U.S. Plant Pat. No. 27,676, 'Chocolate Shogun' U.S. Plant Pat. No. 26.430, *A. chinensis* 'Maggie Daley' (not patented), and *A. chinensis* 'Visions' (not patented).

'Amber Moon' has foliage that is chartreuse tinged reddish in the spring, and the flowers are rosy-pink. 'Chocolate Cherry' has dark green foliage with burgundy overtones and the panicles are more reddish colored and more horizontally branched. 'Chocolate Shogun', has dark purplish-brown foliage and the flowers are pale pinkish-white on more horizontally branched panicles. 'Maggie Daley' has dark green foliage and bright lavender-purple flowers. 'Visions' has medium green foliage with raspberry-pink flowers.

'Dark Side of the Moon' has fewer inflorescences per plant that are taller, longer and broader, and the branchlets are more horizontal, the foliage is a darker greyed-purple with less reddish coloring, and the new plant has a faster growth rate. 'Delft Lace' flowers later in the season, the inflorescence is more airy, and the foliage is more dark-green and less greyed-purple.

BRIEF DESCRIPTION OF THE DRAWINGS

The photographs of the new plant demonstrate the overall appearance of *Astilbe* 'Dragon's Lair' including the unique traits. The colors are as accurate as reasonably possible with modern color reproductions. Some slight variation of color may occur as a result of lighting quality, intensity, wavelength, and direction or reflection. The photographs are of a three-year-old plant grown in a full-sun display garden.

DETAILED BOTANICAL DESCRIPTION

Figure 1:
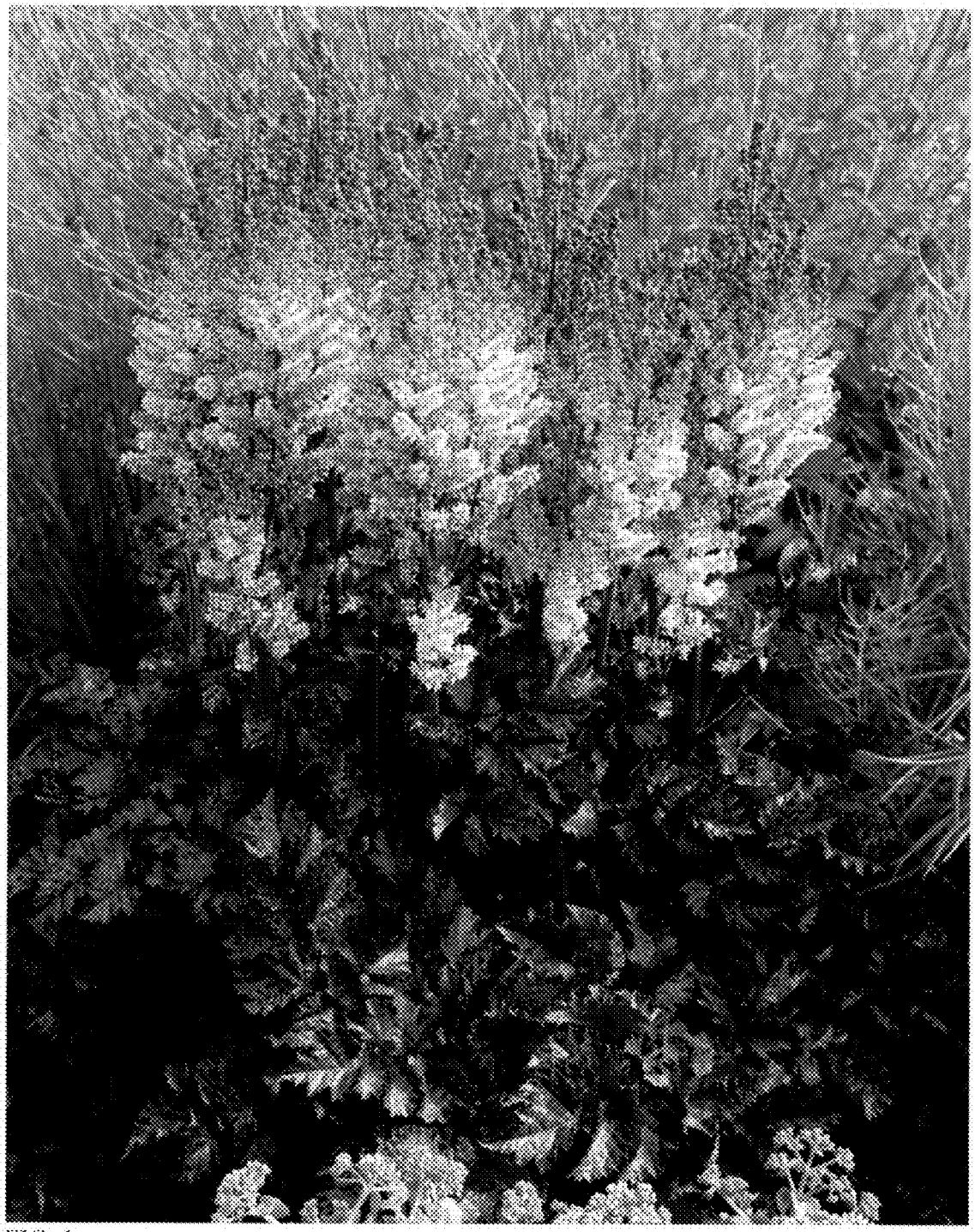
FIG. 1 shows a plant in peak flowering season with foliage.
Figure 2:
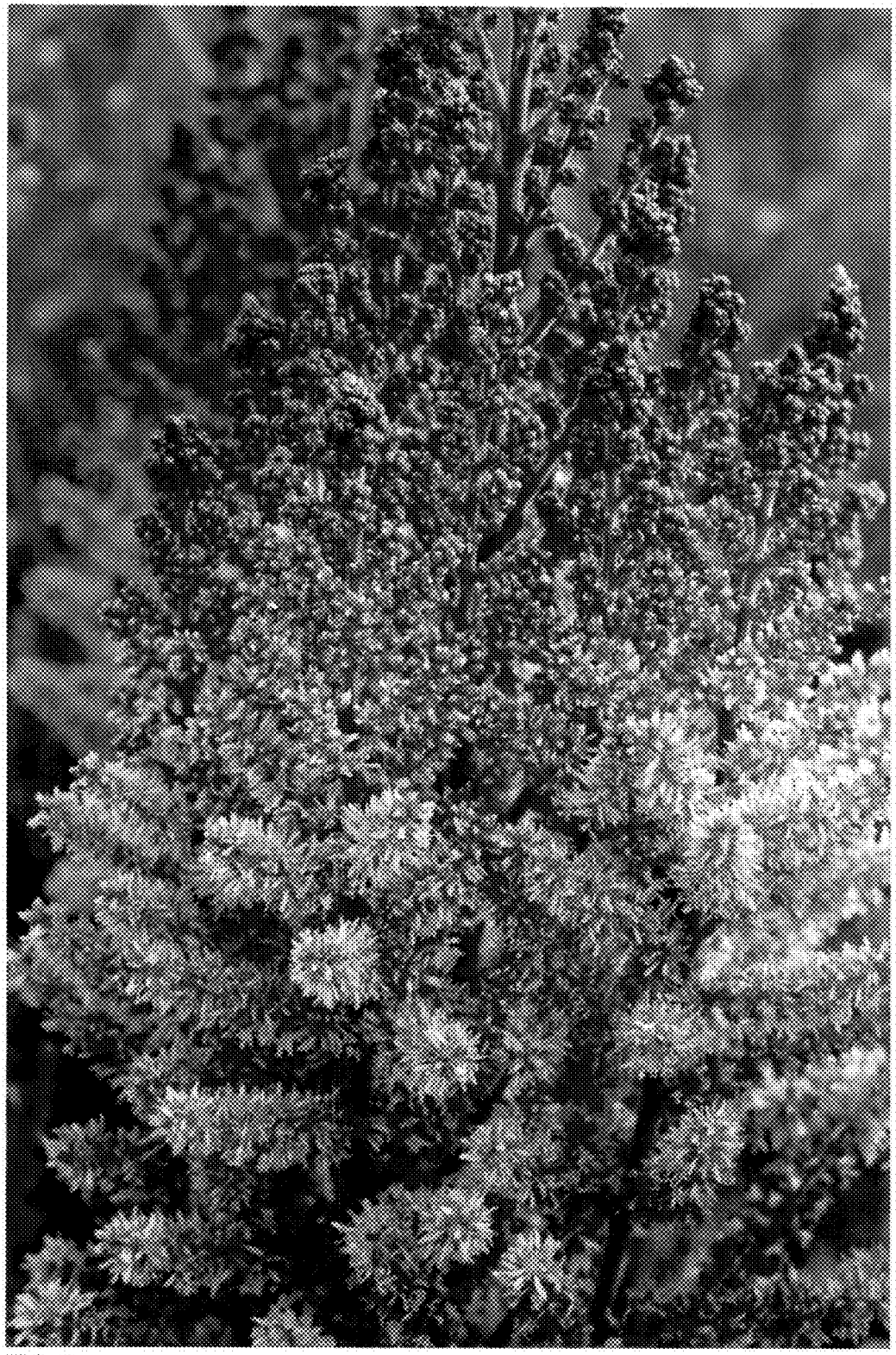
FIG. 2 shows a close-up of the flowering stem with flowers and buds.

The following description is based on three-year-old plants growing in a full-sun outdoor display garden in Zeeland, Michigan, USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Botanical classification: *Astilbe* hybrid;

Parentage: Female parent is *Astilbe* 'Dark Side of the Moon', male parent is 'Delft Lace';

Propagation: By crown division and shoot tip tissue culture;

Time to initiate roots: About three weeks at temperatures about 20° C.;

Root description: Freely-branching; dense; becoming thick, fleshy; color of the roots is dependent on age, substrate composition, water quality, fertilizer type, and formulation; color typically young roots NN155B, older roots nearest RHS 166B;

Plant habit: Herbaceous winter-hardy perennial; broadly mounding plant form with inflorescences held well above the foliar plane; flowering stems and leaves basal;

Growth rate: Rapid; from 25 cm plug finishing in about two months to produce fully-grown flowering plants in 3.8-liter container;

Plant size: Foliage to about 57 cm tall and 88 cm wide; flowering in panicles to about 84 cm tall and about 49 cm wide;

Stem description: About 10 per plant; with cauline leaves in the basal 35 cm and 10 mm diameter at base; erect; strong; stiff; puberulent;

Internode length: About 7 cm;

Stem color: Nearest RHS N186B in high light exposure and nearest RHS 187C in lower light exposure;

Leaf description: Alternate; triternate or tripinnately compound, leaflets three with three leaflet sections on each and proximal pinnule of center pinna with five pinnule; moderately folded longitudinally along midrib, not flat; foliate portion to 30 cm long and 31 cm wide; main lateral pinna to 15 cm long and 14.5 cm wide with each lateral pinnula to 5.2 cm long and 4 cm wide, and terminal pinnula to 5.6 cm long and 4.5 cm wide; main terminal pinna to 17 cm wide and 18 cm long; terminal sub-leaflets to 11.5 cm wide and 11 cm long;

Pinnula: Ovate; apex acute; base attenuate to cordate; margin irregularly to compound crenate and finely apiculate; adaxial surface lustrous and sparsely setulose, abaxial glabrous and matte;

Pinnula color: Expanding adaxial between RHS NN137B and RHS NN137C with moderate blush to solid nearest RHS 187A along margin, developing abaxial nearest RHS 147B with blush to solid margins of nearest RHS 187A; mature adaxial nearest RHS 187A with an undertone of nearest RHS NN137A, mature abaxial between RHS 184B and RHS 183B;

Pinnula venation: Palmate; adaxial impressed, sparsely setulose; abaxial costate and setulose;

Pinnula vein color: Adaxial expanding nearest RHS 146C, abaxial expanding midrib and primary veins nearest RHS N148B and secondary veins nearest RHS 147B; adaxial mature nearest RHS 187A with an undertone of nearest RHS NN137A, abaxial mature midrib and primary veins nearest RHS 187C and secondary veins between RHS 184B and RHS 183B;

Petiole: Cylindrical with single narrow furrow; setulose proximally, becoming sparsely setulose distally; matte; base swollen and clasping; to 24 cm long from base to swollen rachis node and 6 mm diameter above swollen base; distal node swollen to 10 mm across and 8 mm tall; base swollen to about 15 mm tall and 19 mm wide;

Petiole and node color: Adaxial nearest RHS 187B in high light and abaxial nearest RHS 187C; base nearest RHS 187C;

Rachis: Cylindrical with single furrow; sparsely setulose; two side rachises to about 72 mm long and 2 mm diameter at base, central rachis to about 105 mm long to initial branch and 50 mm diameter near middle;

Fragrance: Faint, lightly sweet;

Flowering season: Begin flowering early summer; inflorescence effective for about 14 to 20 days on the plant or as cut flower;

Flower quantity: About 4,000 to 5,000 flowers per inflorescence;

Flower buds one to two days prior to opening: Ellipsoidal to globose; rounded base, acute apex; glabrous, smooth, matte; to about 2.5 mm long and 2 mm diameter;

Flower bud color: Calyx nearest RHS N79C with exserted petals nearest RHS N82B;

Inflorescence: Highly branched panicle; to about 84 cm tall, flowering in upper 35 cm and to about 13 cm wide;

Flower: Perfect; complete; rotate; to about 5 mm across and 4 mm tall;

Petals: Typically, five in a single whorl; oblanceolate; apex rounded; base cuneate; margin entire; glabrous; slightly lustrous; to about 3 mm long and 0.7 mm wide near apex;

Petal color: Adaxial and abaxial RHS NN155D; color just before drying nearest RHS 76C;

Calyx: Campanulate; about 2 mm long and 2 mm across at apex;

Sepals: Typically, five; ovate; about 2 mm long and 1 mm across; apex: acute; basal one-third fused; margin entire; adaxial and abaxial glabrous and lustrous;

Sepal color: Adaxial and abaxial distal one-third to one-half between RHS 60B and RHS 61A; proximal portion transitioning to nearest RHS NN155D; color does not change with development;

Androecium: Typically, ten;

*Filament*.—Cylindrical; straight; about 2.5 mm long and 0.1 mm diameter; hyaline; color nearest RHS NN155D.

*Anther*.—Globose; basifixed; to about 0.5 mm diameter; color prior to dehiscing between RHS 191A and RHS 191B.

*Pollen*.—Not observed.

Gynoecium: Typically, two per flower; about 2.2 mm long;

*Stigma*.—Minute, globose; about 0.2 mm across; color nearest NN155C.

*Style*.—Bifid; to about 2 mm long and 0.5 mm across at base; color between NN155D and RHS 65D.

*Ovary*.—Globose; to about 0.5 mm diameter; color between NN155D and RHS 65D.

Peduncles: Cylindrical; pubescent; matte; to about 84 cm tall and about 7 mm diameter at base; stiff; strong; erect;

Peduncle color: Nearest RHS N186C in flowering portion;

Pedicels: Short; cylindrical; about 0.5 mm. diameter and to about 0.5 mm long;

Pedicel color: Nearest RHS 65D;

Fruit: Bi-valved, dehiscent, ellipsoidal capsule; with acute apiculate apex and acute base; to about 5 mm long and 1.5 mm across near middle; color about RHS N168C as maturing, drying to nearest RHS 200A;

Seeds: Thin, linear; to about 2 mm long and 0.3 mm diameter; color nearest RHS N199B;

Disease and pest resistance: 'Dragon's Lair' has not been noted to be resistant or susceptible to pathogens and pests common to *Astilbe;*

Garden performance: Plants of the new *Astilbe* have been observed to have good garden performance, tolerate strong wind and rain, and are more heat and sunlight tolerant than typical *Astilbe*. The new plant is suitable for at least USDA Hardiness Zones 4 through 9.

It is claimed:

1. A new and distinct *Astilbe* plant named 'Dragon's Lair' as herein described and illustrated.

* * * * *